United States Patent [19]

Schickaneder et al.

[11] Patent Number: 4,647,684

[45] Date of Patent: Mar. 3, 1987

[54] PROCESS FOR THE PRODUCTION OF 4-AMINO-6,7-DIMETHOXY-2-[4-(FURO-2-YL)-PIPERAZIN-1-YL]-QUINAZOLINE AND PHYSIOLOGICALLY COMPATIBLE SALTS THEREOF

[75] Inventors: Helmut Schickaneder, Eckental; Kurt H. Ahrens, Nuremberg, both of Fed. Rep. of Germany

[73] Assignee: Ludwig Heumann & Co. GmbH, Nuremberg, Fed. Rep. of Germany

[21] Appl. No.: 590,231

[22] Filed: Mar. 16, 1984

[30] Foreign Application Priority Data

Nov. 22, 1983 [DE] Fed. Rep. of Germany ..... 83111671

[51] Int. Cl.$^4$ .......................................... C07C 127/26
[52] U.S. Cl. ...................... 558/8; 544/291; 544/398
[58] Field of Search ............. 544/291; 260/465 E; 558/8

[56] References Cited

U.S. PATENT DOCUMENTS 4,001,237 1/1977 Partyka et al. ............... 544/291
4,138,651 2/1979 Crenshaw ................... 544/291
4,578,389 3/1986 Schickaneder et al. ....... 544/291

FOREIGN PATENT DOCUMENTS 0034421 8/1981 European Pat. Off. .
0037971 10/1981 European Pat. Off. .
0146642 7/1985 European Pat. Off. ........ 558/8
79024000 7/1980 Netherlands .
WO7900166 4/1979 PCT Int'l Appl. .

*Primary Examiner*—Glennon H. Hollrah
*Assistant Examiner*—James H. Turnipseed

[57] ABSTRACT

The invention relates to a new multistage process for the production of 4-amino-6,7-dimethoxy-2-[4-(furo-2-yl)-piperazin-1-yl]-quinazoline corresponding to the following formula

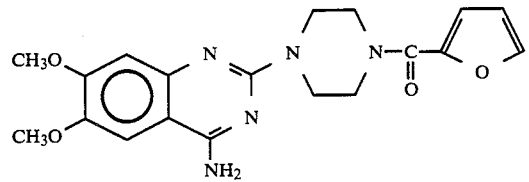

and physiologically compatible salts thereof, which gives better yields and uses less expensive and more reactive materials than known processes. The intermediate product formed in this process, N''-cyano-N'-(3,4-dimethoxyphenyl)-O-phenylisourea, shows antihypertensive activity on its own.

1 Claim, No Drawings

PROCESS FOR THE PRODUCTION OF 4-AMINO-6,7-DIMETHOXY-2-[4-(FURO-2-YL)-PIPERAZIN-1-YL]-QUINAZOLINE AND PHYSIOLOGICALLY COMPATIBLE SALTS THEREOF

DESCRIPTION

This invention relates to a new process for the production of 4-amino-6,7-dimethoxy-2-[4-(furo-2-yl)-piperazin-1-yl]-quinazoline and physiologically compatible salts thereof. This compound, which is known as prazosin, is already known from U.S. Pat. Nos. 3,511,836 and 3,669,968. It is used as a cardiovascular regulator and, in particular, for reducing blood pressure in hypertonic patients.

The invention also relates to the new compound, N''-cyano-N'-(3,4-dimethoxyphenyl)-O-phenylisourea.

South African OPI specification No. 79/1059 describes a process for the production of 4-amino-6,7-dimethoxy-2-[4-(furo-2-yl)-piperazin-1-yl]-quinazoline (prazosin), in which 3,4-dimethoxyaniline is reacted with S,S-dimethyl-N-cyanodithioimidocarbonate to form N-cyano-N'-(3,4-dimethoxyphenyl)-S-methylisothiourea which is then condensed with 1-(furo-2-yl)-piperazine to form 4-(furo-2-yl)-piperazine-1-[N-cyano-N'-(3,4-dimethoxyphenyl)]-carboximide amide which, in turn, is closed at 180° C. to form the 4-amino-6,7-dimethoxy-2-[4-(furo-2-yl)-piperazin-1-yl]-quinazoline ring.

The object of the invention is to improve the known processes for producing prazosin and, more particularly, to provide a new process for its production which may be carried out using less expensive and more reactive materials.

According to the invention, this object is achieved by (a) reacting 3,4-dimethoxyaniline corresponding to the following formula

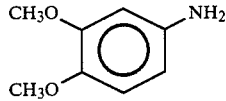
(II)

with N-cyanodiphenylimidocarbonate corresponding to the following formula

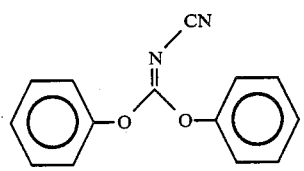
(III)

to form N''-cyano-N'-(3,4-dimethoxyphenyl)-O-phenylisourea corresponding to the following tautomeric formulae

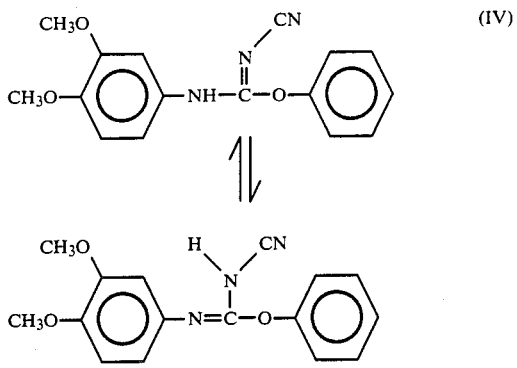
(IV)

(b) reacting the compound obtained corresponding to tautomeric formulae IV with piperazine to form piperazino-1-[N''-cyano-N'-(3,4-dimethoxyphenyl)]-carboximide amide corresponding to the following tautomeric formulae

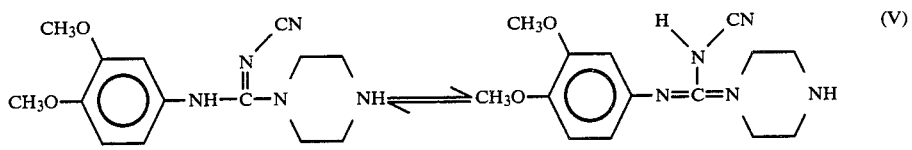
(V)

(c) subsequently cyclizing the compound obtained under acidic conditions to form the salt of 4-amino-6,7-dimethoxy-2-piperazinoquinazoline corresponding to the following formula

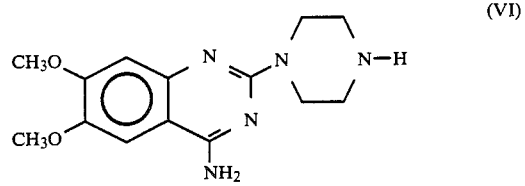
(VI)

(d) forming the free base VI from the salt obtained in stage (c) by reaction with alkali;

(e) reacting the free base with 2-furan carboxylic acid chloride to form 4-amino-6,7-dimethoxy-2-[4-(furo-2-yl)-piperazin-1-yl]-quinazoline hydrochloride; and optionally (f) converting the hydrochloride obtained in stage (e) in known mannr into another physiologically compatible salt.

The invention is based on the surprising discovery that the reaction of 3,4-dimethoxyaniline with N-cyanodiphenylimidocarbonate results in the formation of a new N''-cyano-N'-(3,4-dimethoxyphenyl)-O-phenylisourea derivative which is suitable for use as an intermediate product for producing prazosin in an improved yield under mild reaction conditions (if desired in a one-pot process) using simple production and purification processes. In addition, the use of the inexpensive and more reactive N-cyanodiphenylimidocarbonate instead of the more expensive S,S-dimethyl-N-cyanodithioimidocarbonate represents an economic advantage.

Another advantage of the process according to the invention lies in the fact that, in contrast to the processes mentioned above, no toxic, foul-smelling methyl mercaptan is given off.

The individual stages involved in the process according to the invention are described in detail in the following.

zine to form piperazino-1-[N''-cyano-N'-(3,4-dimethoxyphenyl)]-carboximide amide corresponding to tautomeric formulae V:

$$\text{(V)}$$

Ist stage (a):

In a first stage, 3,4-dimethoxyaniline corresponding to the following formula $$\text{(II)}$$

is reacted with equimolar quantities of N-cyanodiphenyl-imidocarbonate corresponding to the following formula $$\text{(III)}$$

[R. L. Webb, C. S. Labaw, J. Heterocyclic Chem. 19, 1205 (1982)].

The reaction may be carried out in an alkanol, for example isopropanol, at a temperature between 20° C. and the reflux temperature of the solvent. The reaction takes between 1 and 2 hours, depending on the temperature.

For quantitatively producing N''-cyano-N'-(3,4-dimethoxyphenyl)-O-phenylisourea corresponding to the following tautomeric formulae $$\text{(IV)}$$

the reaction is carried out for 80 minutes in isopropanol at reflux temperature.

As mentioned above, N''-cyano-N'-(3,4-dimethoxyphenyl)-O-phenylisourea may exist in the tautomeric forms IV, depending on the solvent used. Accordingly, the process according to the invention also comprises production of the second isomeric form.

IInd stage (b):

In the second stage, N''-cyano-N'-(3,4-dimethoxyphenyl)-O-phenylisourea corresponding to tautomeric formulae IV reacts quantitatively with excess piperazine to form piperazino-1-[N''-cyano-N'-(3,4-dimethoxyphenyl)]-carboximide amide corresponding to tautomeric formulae V:

The reaction is carried out in an alkanol, piperazine being added in excess as reactant, preferably in a molar ratio of 1 to 3. The preferred solvent is isopropanol, in which case the reaction temperature is between 20° C. and 82° C. and preferably is 82° C. The reaction takes between 30 minutes and 1 hour, depending on the temperature.

IIIrd stage (c):

The conversion of piperazino-1-[N''-cyano-N'-(3,4-dimethoxyphenyl)]-carboximide amide corresponding to tautomeric formulae V to form 4-amino-6,7-dimethoxy-2-piperazinoquinazoline corresponding to the following formula $$\text{(VI)}$$

is carried out by cyclization under acidic conditions. Any acids, including Lewis acids, may be used for this purpose. Very good results are obtained, for example, with a 10% aqueous or isopropanolic HCl-solution, the HCl-solution being used for example in a 10-fold molar excess. The cyclization reaction may be carried out at a temperature in the range from 20° C. to 100° C., preferably at a temperature in the range from 50° C. to 100° C. and, more preferably, at a temperature of 50° C. The reaction takes between 20 and 120 minutes, depending on the temperature.

If the cyclization reaction is carried out in isopropanol, 2 to 10 times the molar quantity of HCl gas is introduced into the reaction solution which is then left to react for 1.5 hours at 50° C.

The salt of the acid used, for example the hydrochloride, is obtained in this stage.

As mentioned above, stages (a) to (c) may be carried out, if desired, in a one-pot process.

IVth stage (d):

The free base of formula VI is liberated and isolated from the salt obtained in stage (c), for example the hydrochloride, by the addition of a 2 to 12-fold molar excess of aqueous alkali, for example sodium hydroxide, at room temperature.

Vth stage (e):

The acylation of 4-amino-6,7-dimethoxy-2-piperazino-quinazoline corresponding to formula VI to form the 4-amino-6,7-dimethoxy-2-[4-(furo-2-yl)-piperazin-1-yl]-quinazoline hydrochloride corresponding to formula I is carried out with 2-furan carboxylic acid chloride at 25° C. in an alkanol, such as methanol, ethanol or isopropanol, the yield obtained being substantially quantitative.

The hydrochloride obtained in stage (e) of the 4-amino-6,7-dimethoxy-2-[4-(furo-2-yl)-piperazin-1-yl]-quinazoline may if desired be converted into another physiologically compatible salt in known manner. This salt may be derived, for example, from a mineral acid, such as hydrobromic acid and hydriodic acid, phosphoric acid, metaphosphoric acid, nitric acid or sulfuric acid, or from an organic acid, such as formic acid, acetic acid, propionic acid, phenylacetic acid, tartaric acid, citric acid, furmaric acid, methane sulfonic acid, pamoaic acid, etc. To this end, the hydrochloride obtained in stage (e) is converted back into the base of formula I with alkali, after which the base is reacted with the corresponding acid in known manner to form the required physiologically compatible salt.

For administration, the compound obtained by the process according to the invention may be formulated in the same way as prazosin and its salts, particularly the hydrochloride.

It has surprisingly been found that the compound formed as intermediate product in the process according to the invention, namely N″-cyano-N′-(3,4-dimethoxyphenyl)-O-phenylisourea, shows antihypertensive activity on its own. This was demonstrated using spontaneously hypertensive rats (Dr. Ivanovas Co., Kisslegg). Blood pressure was measured nonoperatively by means of a BP recorder (type 8005, W+W electronic AG, Basel).

An average systolic blood pressure value of 125±6 mmHg (n=10) was recorded in healthy rats (SIC50, Dr. Ivanovas Co., Kisslegg, 160 to 180 g). The antihypertensive effect of the above-mentioned compound was expressed in percent taking the normal systolic value into account, a 100% effect signifying a reduction in blood pressure to the normal level of 125 mmHg.

In a dose of 3 mg/kg p.o., N″-cyano-N′-(3,4-dimethoxyphenyl)-O-phenylisourea produced a 24% normalization and, in a dose of 10 mg/kg p.o., a 42% normalization of the systolic blood pressure of the spontaneously hypertensive rats.

Accordingly, the present invention also relates to the compound N″-cyano-N′-(3,4-dimethoxyphenyl)-O-phenylisourea corresponding to the tautomeric formulae The invention is illustrated by the following Example.

EXAMPLE

Production of 4-amino-6,7-dimethoxy-2-[4-(furo-2-yl)-piperazin-1-yl]-quinazoline hydrochloride

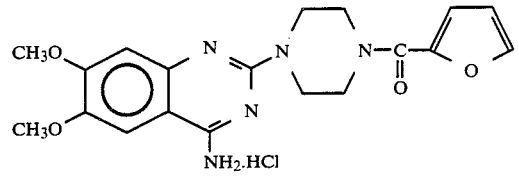

2 g (6.91 mMoles) of 4-amino-6,7-dimethoxy-2-piperazinoquinazoline are suspended in 21 ml of ethanol (p.A.), followed by the addition with vigorous stirring at room temperature of 0.90 g (6.91 mMoles) of 2-furan carboxylic acid chloride. After 3 h, the product precipitated is filtered off under suction, recrystallized from methanol (p.A.) and dried at 100° C.

Yield: 2.72 g (94%)—melting point: 276°-277° C.

Rf-value: 0.62 (ethylacetate/MeOH/HN($C_2H_5$)$_2$ 70:20:5).

$C_{19}H_{22}O_4N_5Cl$ (419.9) calculated: C 54.34, H 5.28, N 16.68, Cl 8.44, observed: C 54.48, H 5.18, N 16.41, Cl 8.37.

$^1$H-NMR-data: (d$_6$-DMSO, TMS as internal standard) δ=3.86 (s, broad) (2×OCH$_3$) 6H, 4.03 (m, broad)

8H, 6.67 (m) (aromatic-H) 1H, 7.13 (d) (aromatic-H) 1H, 7.76 (s) (aromatic-H) 1H, 7.83 (s) (aromatic-H) 1H, 7.93 (s) (aromatic-H) 1H, 8.67 (broad) 1H (replaceable by D$_2$O) 9.1 (broad) 2H (replaceable by D$_2$O) ppm.

(a) Production of N″-cyano-N′-(3,4-dimethoxyphenyl)-O-phenylisourea

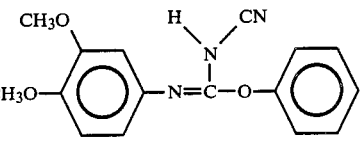

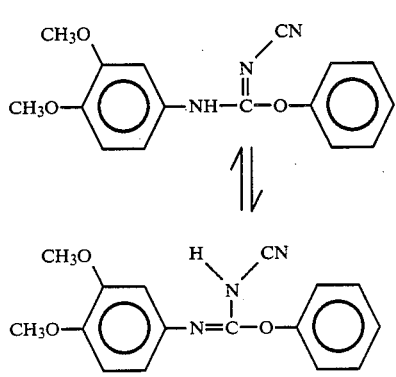

7.66 g (50 mMoles) of 3,4-dimethoxyaniline and 11.91 g (50 mMoles) of N-cyanodiphenylimidocarbonate are dissolved in 50 ml of isopropanol and the resulting solution heated for 80 minutes to reflux temperature. After cooling with stirring, the crystals accumulating are filtered off under suction.

Yield: 13.8 g (93%)—melting point: 163°-164° C.) (decomp.). Rf-value: 0.83 (CH$_2$Cl$_2$/MeOH 9:1).

$C_{16}H_{15}N_3O_3$ (297) calculated: C 64.64, H 5.09, N 14.13, observed: C 64.80, H 5.06, N 13.61.

$^1$H-NMR-data: (d$_6$-DMSO, TMS as internal standard) δ=3.80 (s) (2×OCH$_3$) 6H, 6.83-7.67 (m) (aromatic-H) 8H, 10.5 (s) (N-H) (replaceable by D$_2$O) 1H ppm.

(b) Production of piperazino-1-[N-cyano-N′-(3,4-dimethoxyphenyl)]-carboximide amide

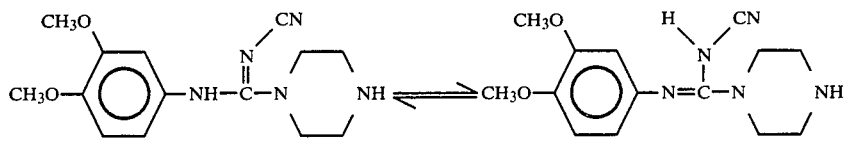

2.50 g (8.4 mMoles) of N''-cyano-N'-(3,4-dimethoxyphenyl)-O-phenylisourea and 2.17 g (25.2 mMoles) of piperazine are heated for 30 minutes in isopropanol to reflux temperature. The product precipitates in crystalline and TLC-pure form.

Yield: 2.18 g (90%)—melting point: 181°–182° C.
Rf-value: 0.24 (MeOH techn.).
$C_{14}H_{19}N_5O_2$ (289)
$^1$H-NMR:data: (d$_6$-DMSO, TMS as internal standard) δ=2.67 (m, broad)

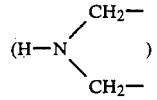

4H, 3.40 (m, broad)

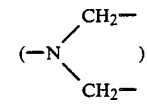

4H, 3.73 (s) (2×OCH$_3$) 6H, 6.50–7.00 (m) (aromatic-H) 3H, 9.00 (broad) (NH) 1H (replaceable by D$_2$O) ppm.

(c) Production of 4-amino-6,7-dimethoxy-2-piperazinoquinazoline

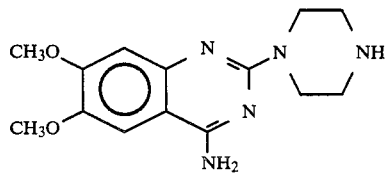

A suspension of 15 g (51.8 mMoles) of piperazino-1-[N''-cyano-N'-(3,4-dimethoxyphenyl)]-carboximide amide is heated for 1.5 h to reflux temperature in 200 ml of 10% aqueous HCl solution. After cooling, the hydrochloride is filtered off, washed with EtOH and dried (M.p. 270°–275° C.). The salt is suspended for 30 minutes in 300 ml of 2N NaOH, after which the product is filtered off and recrystallized from 95% EtOH.

Yield: 11.2 g (75%)—melting point: 230°–232° C.
Rf-value: 0.07 (MeOH techn.).
$C_{14}H_{19}N_5O_2$ (289).
$^1$H-NMR-data: (d$_6$-DMSO, TMS as internal standard) δ=2.67 (m, broad)

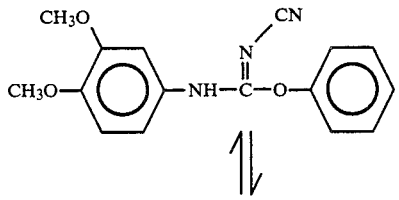

4H, 3.45 (broad) (═N—H) 1H (replaceable by D$_2$O), 3.60 (m, broad)

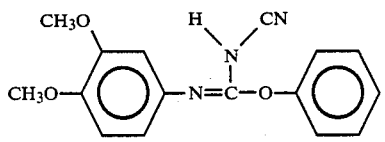

4H, 3.73 (s) (—OCH$_3$) 3H, 3.78 (s) (—OCH$_3$) 3H, 6.63 (s) (aromatic-H) 1H, 7.04 (s) broad (—NH$_2$) 2H, (replaceable by D$_2$O), 7.37 (s) (aromatic-H) 1H ppm.

The one-pot process produced a total yield of 4-amino-6,7-dimethoxy-2-piperazinoquinazoline of 78% of the theoretical.

We claim:
1. N'''-cyano-N'-(3,4-dimethoxyphenyl)-O-phenylisourea corresponding to the following tautomeric formulae